(12) United States Patent
Zhang et al.

(10) Patent No.: US 8,377,895 B2
(45) Date of Patent: Feb. 19, 2013

(54) **CYCLIN-DEPENDENT PROTEIN KINASES INHIBITORS OF *SCUTELLARIA* FLAVONOID ORGANIC AMINE DERIVATIVES, SYNTHESIS AND USE THEREOF**

(76) Inventors: Shixuan Zhang, Dalian (CN); Yongming Bao, Dalian (CN); Yuming Sun, Dalian (CN); Kangjian Li, Dalian (CN); Liang Zou, Dalian (CN); Jigang Ma, Dalian (CN); Xiaodan Sun, Dalian (CN); Haiyan Shang, Dalian (CN); Jing Li, Dalian (CN)

( * ) Notice: Subject to any disclaimer, the term of this patent is extended or adjusted under 35 U.S.C. 154(b) by 46 days.

(21) Appl. No.: 12/676,121

(22) PCT Filed: Jul. 7, 2009

(86) PCT No.: PCT/CN2009/072669
§ 371 (c)(1),
(2), (4) Date: Mar. 2, 2010

(87) PCT Pub. No.: WO2010/003369
PCT Pub. Date: Jan. 14, 2010

(65) Prior Publication Data
US 2010/0197619 A1    Aug. 5, 2010

(30) Foreign Application Priority Data

Jul. 10, 2008    (CN) .......................... 2008 1 0012284

(51) Int. Cl.
*A61K 31/7048*    (2006.01)
*C07H 17/06*    (2006.01)
*A61P 35/00*    (2006.01)
*A61P 31/18*    (2006.01)

(52) U.S. Cl. ............................................. 514/27; 536/8

(58) Field of Classification Search .................. None
See application file for complete search history.

(56) References Cited

PUBLICATIONS

Bablich et al., caplus an 1906:63623.*
Gao et al., caplus an 2004:713279.*
CDK_inhibitor, 2011, http://en.wikipedia.org/wiki/CDK_inhibitor.*
Babu et al., Bioorg. Med. Chem. Lett., 18, 2008, 1659-1662.*

* cited by examiner

*Primary Examiner* — Sun Jae Loewe
(74) *Attorney, Agent, or Firm* — Squire Sanders (US) LLP

(57) ABSTRACT

The present invention provides a series of cyclin-dependent protein kinases (Cdks) inhibitors, *Scutellaria* flavonoid organic amine derivatives, synthesis and use thereof. The preparation method is as follows: taking Baicalein (or Wogonin) from *Scutellaria baicalensis* as lead compound, mixing it with formaldehyde solution and organic amine compounds based on the molar ratio of 1:1-1.2:1-1.2, adding methanol of duplicate weight than baicalein and reacting at 50-70° C., filtering the sediment and washing and then drying so as to get the product with a content of not less than 97% (weight). Similar to Flavopiridol and P276-00, the activity of baicalein organic amine derivatives inhibiting Cdks has an increase of 50 times compared with that of Baicalin. It can selectively induce apoptosis of the proliferative phase cancer cells, which has scarcely any influence to the normal structure, and it belongs to anticancer drugs of cell cycle inhibitor kind. The product has a rich source of raw materials and has simple process, high purity, low cost, clear metabolic mechanism, high efficiency and low toxicity, which can be made into oral preparations or injections together with acid salts and is expected to become high efficient and low toxicity anti-cancer and AIDS drugs.

14 Claims, 1 Drawing Sheet

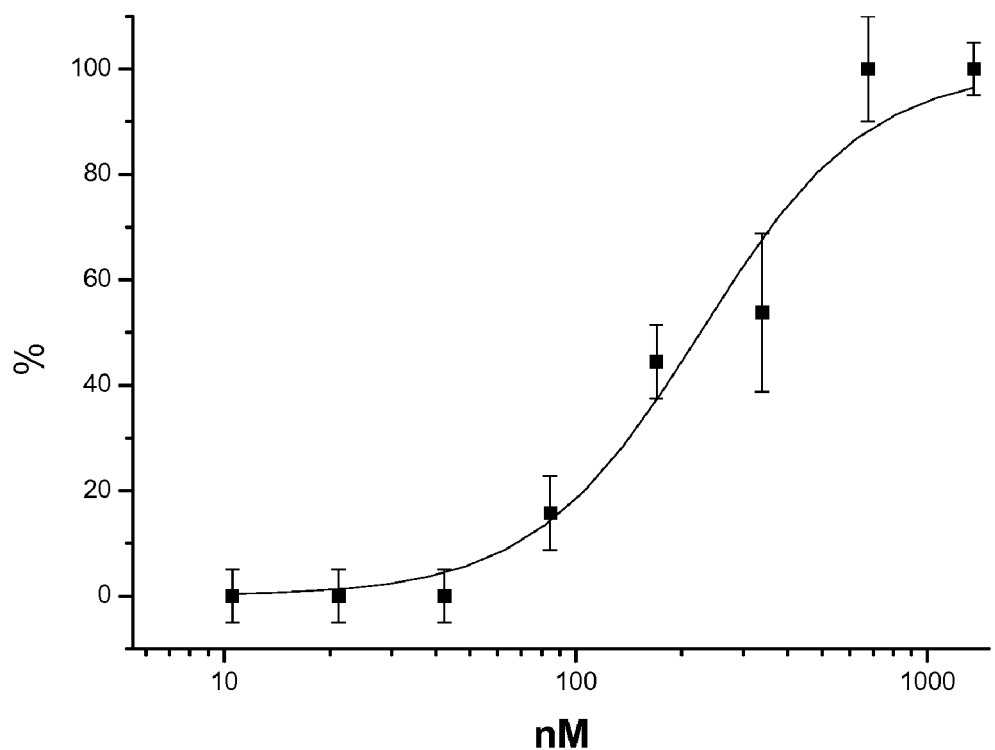

CYCLIN-DEPENDENT PROTEIN KINASES INHIBITORS OF *SCUTELLARIA* FLAVONOID ORGANIC AMINE DERIVATIVES, SYNTHESIS AND USE THEREOF

FIELD OF THE INVENTION

The present invention relates to the field of drug synthesis. More particularly, it relates to synthesis of a series of cyclin-dependent protein kinases inhibitors, *Scutellaria* flavonoid organic amine derivatives, and their potential applications in anti-cancer and anti-AIDS.

BACKGROUND OF THE INVENTION

Cell cycle regulation is a very complicated and delicate process, containing cell growth, differentiation, proliferation and apoptosis. In the past decades, the discovery in process of cell cycle signal transduction pathway is a great milestone in molecular biology history. Protein kinases regulate many critical biological mechanisms, including metabolism and cell growth, proliferation, and differentiation. Aberrations in the activity of the kinases involved in signal transduction have been linked to many human diseases such as cancer, diabetes and inflammation. More than 600 kinases have been encoded on human genome The cyclin-dependent kinases (Cdks) are a prominent family of protein kinases, which plays a key role in cell-cycle progression and cellular proliferation. Cdks are a serine/threonine protein kinase, multi-subunit enzymes composed of at least a catalytic subunit protein kinases and a regulatory subunit cyclin. Cdks exert their effective activation of host proteins through phosphorylation of key serine or threonine residues by ATP. The phosphorylated proteins modulate the activity of a variety of cellular proteins. Mitosis is activated by the driver of Cdk1/Cyclin B, which has been widely accepted. It has been found that 90% of tumor formation is related to the highly activated Cdks led by Rb tumor suppressor protein phosphorylation, which result Rb-path deactivation. Cdks inhibitor is effective in inducing apoptosis and improving the sensitivity of chemotherapy drugs. Cdks have become attractive therapeutic targets for anti-cancer drug discovery. [Science, 2004, 303, 1800; The AAPS Journal, 2006, 8, E204; Cancer Biology Therapy, 2003, 4, S84]

Natural flavonoids are found in many plants with various biological activities, and are one series of natural Cdks inhibitors. However, natural flavonoids are often poor water soluble, with low bioavailability and Cdks inhibitory activity. In order to enhance potency, structure modification of natural flavonoids is of great importance and value.

In 1994, through globally natural anti-cancer drug screening by U.S. National Cancer Institute (NCI), Rohitukine, which is an alkaloid flavonoid from Indian plant *Dysoxylum binectariferum*, was selected and exhibited moderate anti-cancer activity. Flavopiridol, which is a derivative derived from rohitukine, demonstrated potent Cdks inhibitory activity and low toxicity. Flavopiridol is firstly synthesized by Aventis Corporation, a new amino synthetic derivative of natural flavonoid. Flavopiridol was initially discovered as an anti-proliferative epidermal growth factor receptor kinase inhibitor. Subsequent studies show, however, that Flavopiridol is an even more potent inhibitor of Cdks. In addition, it is also proved to be an mRNA transcription inhibitor. Flavopiridol has been the first anti-cancer drug candidate which targets cell cycle signal transduction, and currently has been in the process of Phase II clinical trial in U.S.A. Iowa State University researchers have found that Flavopiridol may hinder the AIDS virus HIV-1 in the cell proliferation, and significantly increase the sensitivity of chemotherapy drugs. P-TEFb has also been proved to be highly inhibited by Flavopiridol in relative low dose, which also indicates promising prospect in anti-cancer and anti-AIDS therapy. [Cancer Biology Therapy, 2003, 4, S84, 77, 146; Curr. Pharm. Des., 2006, 12, 1949] An interesting finding was that apoptosis inhibitor survivin was Cdk1/Cyclin B phosphorylation, may cancel its anti-apoptotic activity, where as survivin expresses only in malignant tumors, not in mature tissues. Flavopiridol can reduce the concentration of survivin in malignant tumor cells indirectly, through inhibiting Cdk1/Cyclin B. Louis Staudt from NCI revealed that the mechanism of Flavopiridol inducing cancer cell apoptosis and HIV proliferation inhibition was attributed to the blockage of transcription mRNA of most gene, and only targeted anti-cancer cells selectively by the use of DNA chip technology. This is because RNA in the immoderate growing cancer cells is very short-lived, which is totally dependent on the incessant synthesis of mRNA. Once Flavopiridol enter into the cells, the synthesis of mRNA is blocked. Short-lived RNA in cancer cells are degradated rapidly, while the majority of normal cells with long-lived mRNA still exist, so it only induce cancer cells apoptosis selectively. Flavopiridol is a selective Cdks inhibitor interacting specifically with the ATP binding site of Cdks. It inhibits growth of cancer cells through inducting apoptosis, unlike cytotoxic anti-cancer drugs which kill cells directly. It means that although Cdks exists in all series of human cells, cancer cells would be inhibited to grow mostly for their considerable multiplication compared to normal cells. So, less harm would be against the normal human cells. [Genome Biology, 2001, 2 (10), 0041.1] Flavopiridol can also improve the sensitivity of chemotherapy drugs effectively, and has obvious synergies effect and suppression of "multi-drug resistance", which can also be used in advanced staged cancer treatment so as to improve life quality and lengthen life time. However, Flavopiridol is a chiral compound with complex, low yielded and high-cost synthesis processes. Moreover, there is still a severe side effect in its clinical application, such as diarrhea and so on. In a word, the discovery of competitive Cdks-ATP binding site inhibitor Flavopiridol has brought new treatment channel for cancer and AIDS.

In 2008, P276-00, like Flavopiridol, is a novel Cdks inhibitor of organic amine derivatives of flavonoid, currently in phase II clinical trials as a potential anti-cancer agent by Kalpan S. Joshi. [WO2004/004632] However, unlike Flavopiridol, it shows better selectivity toward Cdk1-B, Cdk4-D1, and Cdk9-T1 as compared with Cdk7-H and Cdk2-E. The inhibition to 12 kinds of human tumor cells growth in culture is twice to thrice higher than Flavopiridol, while less toxic than Flavopiridol and almost has no inhibitory activity on two human embryonic normal lung fibroblast WI-38 and MRC-5.

However, similar to Flavopiridol, poor solubility and low bioavailability of P276-00 may affect its effects of Cdks inhibitors. [Molecular Cancer Therapeutics, 2007, 6, 918]

Scutellaria baicalensis Georgi is a kind of the most widely used traditional herbal medicines and plants the largest of cultivated varieties of medicinal herbs in China. As the main active ingredient, Scutellaria flavonoids is as high as 10-20%, with the function of anticancer, antimicrobial, anti-inflammatory, anti-allergic, anti-oxidation, anti-blood fat, anti-thrombosis and so on. As a natural Cdks inhibitor, Baicalein and Wogonin are stronger than Scutellaria flavonoid glycosides. Baicalein and Wogonin can induce apoptosis, inhibit cell proliferation, and inhibit HIV replication and reverse transcriptase. The function of anti-tumor and anti-AIDS and so on suggests that there is a unique role, has been extensive attention. [Cancer Treatment Reviews, 2009, 35, 57] However, skullcap flavonoids are insoluble in water, easily oxidized and low serum concentration of active strength, so they do not reach clinical needs. Therefore, the inventors hope to find new efficient ATP-selective inhibitor of Cdks with low toxicity through structural modification of skullcap flavonoids. The flavonoid derivatives U.S. Pat. No. 5,849,733 disclosed Flavopiridol of thio- and oxo-derivatives as Cdks inhibitors for the treatment of proliferative diseases. CN16686131A (WO2004/004632) disclosed flavonoid derivatives as Cdks inhibitors. U.S. Pat. No. 5,116,954 disclosed with the anti-tumor and immunomodulatory activity of flavonoids. CN1990481 disclosed a kind of baicalein derivatives, their preparation methods and uses. CN1427003A disclosed inhibit the protein kinase C activity of 8-substituted methylamine baicalein derivatives and their preparation methods. The patent did not mention the present invention involved in skullcap flavonoid organic amine derivatives, as well as Cdks inhibitors purposes.

SUMMARY OF THE INVENTION

Our invention is to find new selective Cdks inhibitors with high efficiency and low toxicity through structural modification of Scutellaria flavonoid. The purpose of the present invention is to provide preparation method for Scutellaria flavonoid organic amine derivatives which is a condensation reaction of Baicalein or Wogonin as lead compounds with formaldehyde and organic amine. With organic acid salt and pharmaceutically acceptable excipients, the derivatives can be made into oral supplement or injection with beneficial applications such as formulations drugs, as well as applications in prevention and treatment of cancer and AIDs.

The target compounds of this invention Scutellaria flavonoid organic amine derivatives with the structures illustrated in the following scheme: wherein when R6 is OH, R8 is methylene of piperazine, methylpiperazine, hydroxyethylpiperazine, ethanethiolpiperazine, hydroxylpiperidine, piperidone, hydroxymethylpyrrolidine, hydroxylpyrrolidine, or diethanolamine; when R8 is OCH3, R6 is methylene of piperazine, methylpiperazine, hydroxyethylpiperazine, ethanethiolpiperazine, hydroxylpiperidine, piperidone, hydroxymethylpyrrolidine, hydroxylpyrrolidine, diethanolamine, dimethylamine, pyrrolidine, piperidine, morpholine, or sulfurmorpholine.

Within the scutellaria flavonoid organic amine derivatives described above, the compounds of the following structure are preferred: when R6 is OH, R8 is methylene of hydroxylpiperidine, hydroxyethylpiperazine, ethanethiolpiperazine hydroxylpyrrolidine, or diethanolamine. When R8 is OCH3, R6 is methylene of hydroxyethylpiperazine, hydroxylpiperidine, methylpiperazine, hydroxylpyrrolidine, or diethanolamine.

Particularly, it is preferred that when R6 is OH, R8 is methylene of hydroxylpiperidine, hydroxylpyrrolidine or hydroxyethylperazine; when R8 is OCH3, R6 is methylene of hydroxyethylperazine, hydroxylpiperidine, hydroxylpyrrolidine, or diethanolamine.

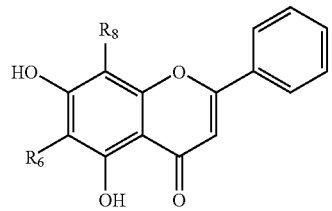

The Solutions of the Invention are as Follows:

Preparation principle of Scutellaria flavonoid organic amine derivatives: Baicalin and wogonoside are the most abundant component in Scutellaria baicalensis in China. Baicalin and wogonoside were hydrolyzed with itself enzyme of Scutellaria baicalensis, and Baicalein and Wogonin were isolated as lead compounds.

The synthesis process of Scutellaria flavonoid organic amine derivatives is as follows: taking Baicalein or Wogonin as lead compound, mixting it with formaldehyde solution and organic amine compounds based on the molar ratio of 1:1-1.2:1-1.2, adding methanol of 10~40 times weight than baicalein or Wogonin, and stirring at 50-70° C. for 1-6 hours, filtering the sediment and washing with methanol of 1~20 times weight than baicalein or Wogonin, and then drying so as to get the product with a content of not less than 97% (weight).

The synthesis process of Scutellaria flavonoid organic amine derivatives, wherein when Baicalein is used, the organic amine is piperazine, methylpiperazine, hydroxyethylpiperazine ethanethiolpiperazine, hydroxyethylpiperazine piperidone, hydroxymethylpyrrolidine, hydroxylpyrrolidine or diethanolamine; when Wogonin is used, the organic amine is piperazine, methylpiperazine, hydroxyethylpiperazine ethanethiolpiperazine, hydroxylpiperidine, piperidone, hydroxymethylpyrrolidine, hydroxylpyrrolidine, diethanolamin, dimethylamine, pyrrolidine, piperidine, morpholine or sulfurmorpholine.

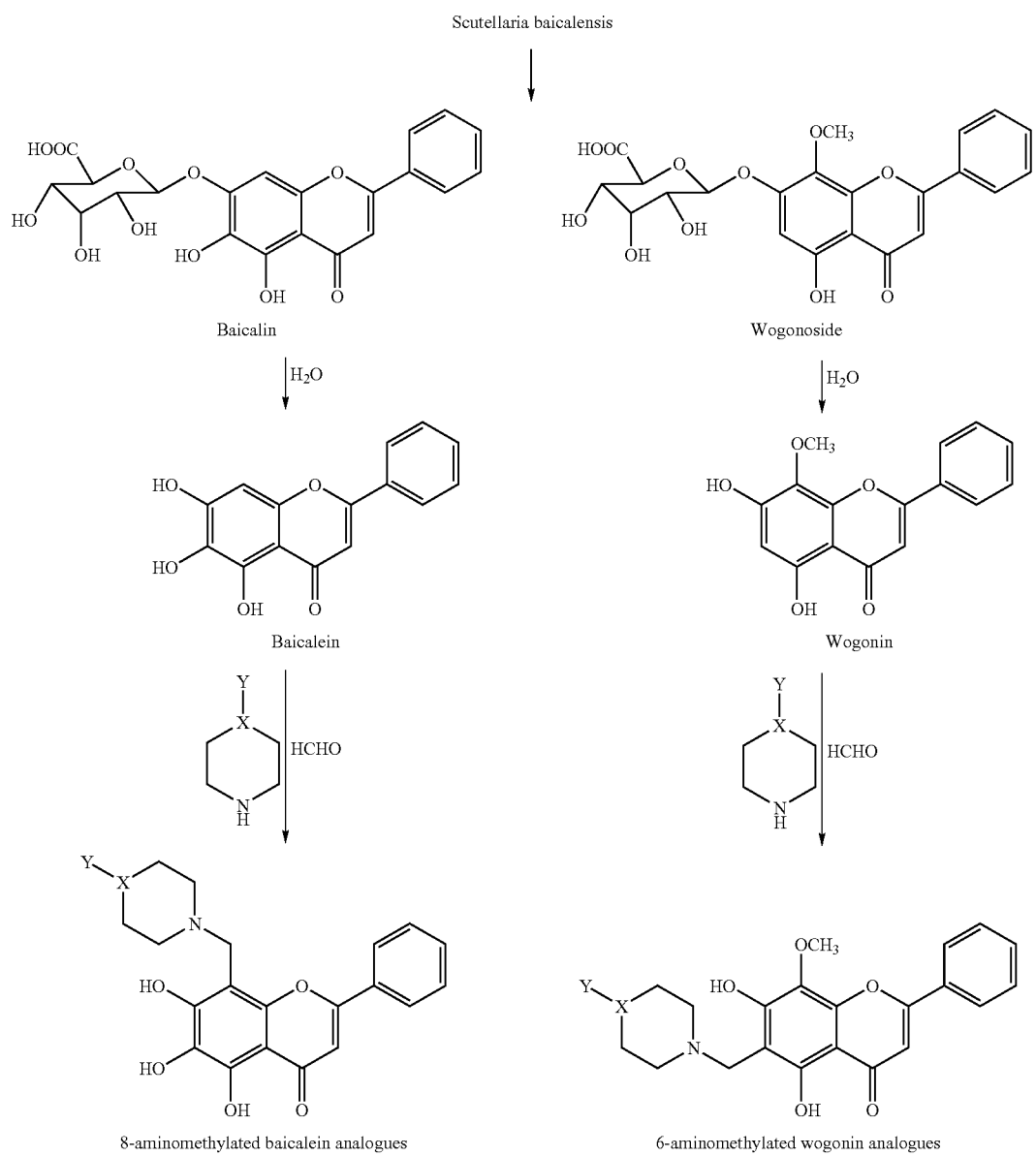

Evaluation of Cdk1/Cyclin B Inhibitory Activity

The Cdk1/Cyclin B enzyme activity was measured by a fluorescence kinetic assay using the Z'-LYTE™ Kinase Assay Kits (Invitrogen Corporation, CA, USA). The Z'-LYTE™ biochemical assay employs a FRET aminomethylated, coupled-enzyme format and is based on the differential sensitivity of phosphorylated and non-phosphorylated peptides to proteolytic cleavage. The assay uses a synthetic peptide substrate (the Z'-LYTE™ Peptide Substrate) that is labeled with a donor fluorophore (coumarin) and an acceptor fluorophore (fluorescein) which makes up a FRET pair. In the primary reaction (the Kinase Reaction), the kinase transfers the γ-phosphate of ATP to a single tyrosine, serine, or threonine residue on the substrate, while the presence of a kinase inhibitor in the primary reaction suppresses phosphorylation. In the secondary reaction (the Development Reaction), a site-specific protease (the Development Reagent) is added at an optimized concentration. The development buffer quenches the Kinase Reaction, while the protease recognizes and cleaves non-phosphorylated Z'-LYTE™ Peptide Substrate at a substantially higher rate than phosphorylated substrate. Cleavage disrupts FRET between the donor and acceptor fluorophores on the non-phosphorylated substrate, while uncleaved, phosphorylated substrate maintains FRET. Concentrations of all reagents are carefully optimized to maximize the assay window for each Z'-LYTE™ Peptide Substrate. Reaction progress is quantified by calculating the emission ratio.

The assay was performed: *Scutellaria* flavonoid organic amine derivatives were solubilized in 1% DMSO and added to the reaction mixture at 8 concentrations of 0.01-25 μM, and ATP 10 μM, Cdk1/Cyclin B activity are controlled in 20-50% of blank-phosphorylated. The biological results of inhibition against Cdk1/Cyclin B of *Scutellaria* flavonoid organic amine derivatives showed that Table 1. Baicalin shows slight inhibition against Cdk1/Cyclin B. Baicalein, hydrolyzed Baicalin, has the inhibitive activity about 9 time higher than that of Baicalin. Baicalein analogues with a heteroatom has the inhibitive activity about 2 times higher than that of Baicalein. Baicalein analogues with two heteroatoms has the inhibitive activity about 5-7 times than that of Baicalin and about 50 times than Baicalein. The mechanism and level are similar to Flavopiridol, which is competitive and selective Cdks-ATP binding site inhibitors, but is different from protein kinases toxic agent Staurosporine. Methylpiperazine Baicalein Cdk1/Cyclin B to inhibitory activity curve is illustrated in FIG. 1. Research shows that *Scutellaria* flavonoid organic amine derivatives have strong inhibitory activity of Cdk1/Cyclin B, and also have a good prospect in the treatment of cancer and AIDS.

SAR studies on flavonoid base derivatives for their Cdk1/Cyclin B inhibitory activity are suggested as follows: (1) The base group of $C_8$, itrogen substituents against Cdk1/Cyclin B inhibitory activity has played a crucial role, and with the increased number of hetero-atoms or the reduced of lipid-water partition coefficient activity was enhanced, due to the base group occupy Cdk1/Cyclin B ATP-binding pocket in the amino-bit reasons. (2) The acidic groups made of $C_4$=0, $C_5$—OH, $C_7$—OH are necessary. If increase $C_6$—OH, the activity is enhanced, while the absence of phenolic hydroxyl, or methylation would affect the inhibitory activity, due to the acidic group occupy for Cdk1/Cyclin B ATP-binding pocket in the phosphate-bit reasons. (3) The hydrophobic group at $C_2$ is necessary, and then the addition of hydrophobic groups such as halogen makes the activity increase, while the hydrophilic hydroxyl groups such as the introduction of activity would affect the inhibitory activity. This fat-soluble group is that the ATP does not have. It might fuse with the hydrophobic pockets of Cdk1/Cyclin B, leading to apparent change in conformation.

Druggability Screening of *Scutellaria* Flavonoid Organic Amine Derivatives:

Include lipid-water partition coefficient, solubility in PBS (pH7.4), protein binding rate, half-life of elimination phase and equilibrium phase of blood drug concentration. The results showed that Table 1, just from the current test results in terms of hydroxypiperidin Baicalein, hydroxyethylpiperazine Baicalein, and hydroxyethylpiperazine Wogonin show good druggability, which implies equilibrium phase of blood drug concentration is about 1000-3000 times higher than the lead compound Baicalein, and increase about 100-300 times compared with the control drug Flavopiridol. In addition, hydroxylpyrrolidine Baicalein and diethanolamine Wogonin also have a certain degree of application prospect. Druggability screening of other organic amines Skullcap flavonoid derivatives is under way.

TABLE 1

Druggability screening of *Scutellaria* flavonoid organic amine derivatives

| *Scutellaria* flavonoid derivatives | Cdk1/ Cyclin B $IC_{50}$ (μM) | MCT-7 $GI_{50}$ (μM) | MCF-7 $LC_{50}$ (μM) | protein binding rate (%) | Solubility in PBS (μM) | Blood drug concentration (μM) | half-life $t_{1/2}$ (h) |
|---|---|---|---|---|---|---|---|
| Baicalin | 18.15 | | | | | | |
| Baicalein | 2.08 | | | | | 0.026 | 5.26 |
| Dimethylamine Baicalein | 1.05 | 12.33 | 37.07 | | | | |
| Pyrrolidine Baicalein | 1.22 | 10.33 | 34.53 | | | | |
| Piperidine Baicalein | 1.28 | 10.50 | 37.17 | | | | |
| Morpholine Baicalein | 0.30 | 10.13 | 48.90 | | | | |
| Sulfurmorpholine Baicalein | 0.38 | 14.17 | 84.33 | | | | |
| Piperazine Baicalein | 0.28 | 13.80 | 53.10 | | 166 | | |
| Methylpiperazine Baicalein | 0.29 | 10.90 | 37.23 | 98 | 6.02 | | |
| Hydroxypiperidin Baicalein | 0.30 | 10.21 | 40.05 | 91 | 377 | 28.7 | 4.23 |
| Hydroxyethylpiperazine Baicalein | 0.28 | 13.1 | 42.10 | 96 | 607 | 31.6 | 3.75 |
| Hydroxylpyrrolidine Baicalein | 0.29 | | | | | | |
| 6-$OCH_3$— Methylpiperazine Baicalein | 0.88 | 26.10 | >100 | | | | |
| Wogonin | 3.50 | | | | | | |
| Dimethylamine Wogonin | 7.63 | | | | | | |
| Pyrrolidine Wogonin | 17.21 | | | | | | |
| Piperidine Wogonin | 10.50 | | | | | | |
| Morpholine Wogonin | >25 | | | | | | |
| Sulfurmorpholine Wogonin | 3.17 | | | | | | |
| Piperazine Wogonin | 6.62 | | | | | | |

TABLE 1-continued

Druggability screening of *Scutellaria* flavonoid organic amine derivatives

| *Scutellaria* flavonoid derivatives | Cdk1/ Cyclin B $IC_{50}$ (μM) | MCT-7 $GI_{50}$ (μM) | MCF-7 $LC_{50}$ (μM) | protein binding rate (%) | Solubility in PBS (μM) | Blood drug concentration (μM) | half-life $t_{1/2}$ (h) |
|---|---|---|---|---|---|---|---|
| Methylpiperazine Wogonin | >25 | | | | | | |
| Hydroxypiperidine Wogonin | 6.91 | | | | | | |
| Hydroxyethylpiperazine Wogonin | 0.32 | 11.1 | 43.10 | | 9390 | 94.0 | 4.00 |
| Diethanolamin Wogonin | 0.31 | | | | | | |
| Flavopiridol | 0.30 | 0.048 | 35.90 | | | 0.271 | 3.60 |
| P276-00 | 0.79 | | | | | | |

(Note: Blank space no determination)

Methylpiperazine Baicalein Inhibits Cancer Cell Growth and Induced Apoptosis:

Methylpiperazine Baicalein $IC_{50}$ against human cervical carcinoma HeLa cell line, human breast cancer MCF-7 and human gastric cancer BGC823 cell lines were determined at 24, 48 and 72 hour through MTT method. At concentration equals to $IC_{50}$, early apoptosis was evaluated at 48 hours through Annexin V-PI double staining flow cytometry analysis. The results show that methylpiperazine Baicalein had potent inhibitory activity on cancer cell growth and induced cell apoptosis by Cdks inhibitory, which induced apoptosis in early stage cancer is much greater than the proportion of late, including Cdks inhibition is a key mechanism for inducing apoptosis, in the medical treatment can be used to prepare anti-cancer drug. (Table 2)

TABLE 2

Methylpiperazine Baicalein on inhibit cancer cell growth and induced apoptosis

| $IC_{50}$ (μM) | HeLa | MCF-7 | BGC823 |
|---|---|---|---|
| 24 h | 12.8 ± 0.20 | 13.7 ± 0.21 | 9.6 ± 0.21 |
| 48 h | 8.2 ± 0.15 | 10.6 ± 0.17 | 7.2 ± 0.23 |
| 72 h | 6.7 ± 0.24 | 7.4 ± 0.25 | 6.5 ± 0.19 |
| early apoptosis (%) | 67.3 | 72.3 | 69.2 |
| late apoptosis and cellular necrosis (%) | 27.1 | 23.1 | 22.2 |

Anticancer activity of methylpiperazine Baicalein, hydroxyethylperazine Baicalein, hydroxypiperidin Baicalein and 6-OCH$_3$—Methylpiperazine Baicalein were evaluated in human Breast (MCF-7), gastric (BGC-823), and Prostate (PC-3) cervical cancer cell lines at 48 h. (Table 3), while the analogues 100 μM on the two kinds of normal human embryonic lung fibroblasts WI-38 and HLF in vitro growth rate of 48 hours, basically consistent with the blank control group, no significant difference. Anticancer activity of methylpiperazine Baicalein, hydroxyethylpiperazine Baicalein and hydroxypiperidin Baicalein were evaluated, with growth inhibition rates in vitro 58 kinds human tumor cell for 48 h at 10 μM were 50.0%, 46.2%, 40.6%, respectively by NCI. The results showed that: The analogues have obvious anti-tumor activity, but have scarcely any influence to the normal tissue cells. Anticancer activity of 6-methoxy-methylpiperazine Baicalein, with the metabolite of methylpiperazine Baicalein, is reduced.

TABLE 3

Anticancer activity of aminomethylated Baicalein analogues in vitro

| Cancer | μM | Methylpiperazine Baicalein | Hydroxyethylpiperazine Baicalein | hydroxypiperidin Baicalein | 6-OCH$_3$-Methylpiperazine Baicalein |
|---|---|---|---|---|---|
| PC-3 | IC50 | 21.1 | 11.6 | 18.1 | 87.6 |
|  | GI50 | 8.2 | 6.2 | 6.0 | 11.2 |
|  | TGI | 19.8 | 15.4 | 16.4 | 76.1 |
|  | LC50 | 38.8 | 36.6 | 41.0 | |
| BGC-823 | IC50 | 23.1 | 19.3 | 18.6 | 114.7 |
|  | GI50 | 6.4 | 6.1 | 5.7 | 26.2 |
|  | TGI | 19.8 | 15.4 | 16.4 | |
|  | LC50 | 62.7 | 51.0 | 53.1 | |
| MCF-7 | IC50 | 19.3 | 20.4 | 20.1 | |
|  | GI50 | 6.4 | 6.0 | 6.0 | |
|  | TGI | 16.4 | 15.4 | 16.4 | |
|  | LC50 | 31.3 | 32.6 | 31.0 | |

Induction $CD_4^+T$ Lymphocytes of Apoptosis:

The differentiate growth inhibition rates of $CD_4^+T$ lymphocytes in 48 h were 55.0% and 46.2%, in 10 μM hydroxyethylperazine Wogonin and hydroxypiperidin Baicalein by the growth factor IL-3 and IL-5 so induced. The results showed that hydroxyethylperazine Wogonin and hydroxypiperidin Baicalein can induce apoptosis of $CD_4^+T$ lymphocytes, and also can induce the apoptosis of HIV-infected $CD_4^+T$ lymphocyte, in which Cdks inhibition is the key of this induction of apoptosis. These show a good prospect against AIDS, and are going to be prepared anti-AIDS drugs. The Major Metabolic Process of Methylpiperazine Baicalein in Rabbits:

High-performance liquid chromatogram-DAD-MS (LC-DAD-MS) test results showed that methylpiperazine Baicalein is rapidly distributed to various tissues, and is highly bound to plasma (98%) in a dose-independent manner. The major metabolic process relates to the structures is illustrated in the following scheme.

acid or inorganic acid, such as the *Scutellaria* flavonoids organic amine mesylate or phosphate. Oral preparations and injections of the *Scutellaria* flavonoids organic amine mesylate are going to be used for the treatment of cancer and AIDS. The Outstanding Advantages of this Invention Compared with the Existing Technology:

This invention provides a series of Cdks inhibitors, *Scutellaria* flavonoid organic amine derivatives, synthesis and use thereof. The skullcap flavonoids as the leading compounds were extracted and isolated from traditional Chinese medicine *Scutellaria baicalensis*. *Scutellaria* flavonoid organic amine derivatives were obtained by condensation reaction of leading compounds, formaldehyde and organic amine. Preliminary studies have shown that Similar to Flavopiridol and P276-00, the activity of baicalein organic amine derivatives inhibiting Cdks has an increase of 50 times compared with that of Baicalin. It can selectively induce apoptosis of the proliferative phase cancer cells and differentiate growth of CD4+ T lymphocytes, but has scarcely any influence to the

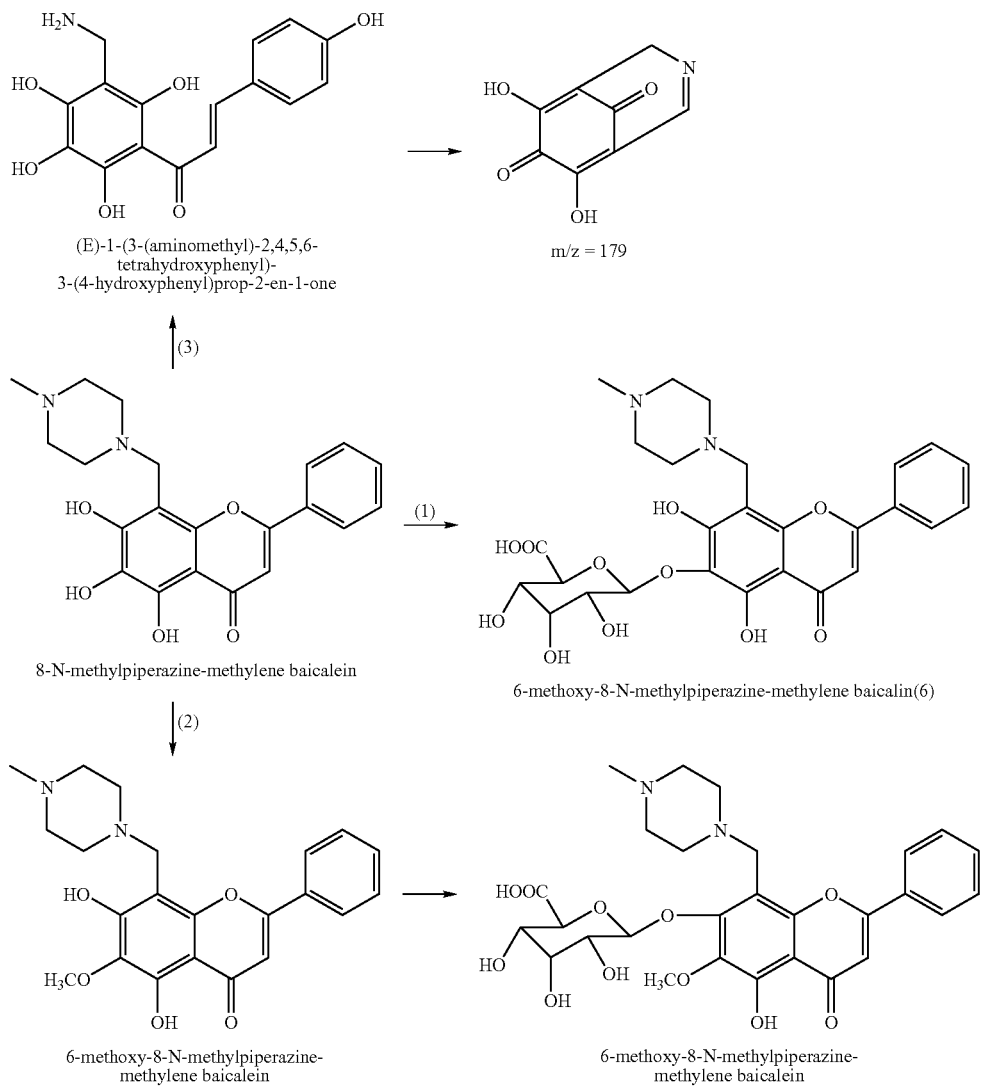

*Scutellaria* flavonoid organic amine derivatives salts were made of high-purity series *Scutellaria* flavonoid organic amine derivatives with pharmaceutical acceptable organic normal structure, and it belongs to anticancer drugs of cell cycle inhibitor kind. The product has a rich source of raw materials and has simple process, high purity, low cost, clear metabolic mechanism, high efficiency and low toxicity, which can be made into oral preparations or injections together with acid salts and is expected to become high efficient and low toxicity anti-cancer and AIDS drugs.

FIGURE DESCRIPTION

On FIG. 1, A measured curve of methylpiperazine baicalein on Cdk1/Cyclin B inhibitory activity, the abscissa for the methylpiperazine baicalein concentration (nM), the vertical axis for the right Cdk1/Cyclin B activity inhibition rate (%).

EXAMPLES

Examples 1

Preparation of 5,6,7-trihydroxy-8-((4-methylpiperazin-1-yl)methyl)-2-phenyl-4H-chromen-4-one [Methylpiperazine Baicalein]

The mixture of Baicalein (100 g), methanol 2 L, 37% formaldehyde solution (36.5 ml), 4-N-methyl-piperazin solution (45 g) was stirred under for 4 hours at 55° C., then precipitates were removed by filtration and washed several times with methanol, after drying under reduced pressure at 55° C. to get the product as yellow solid 113 g of purity 99.9%. m.p.: 280~282° C. UV: λmax(alcohol) 278, 330 nm; MS: (API-ES) m/z 383.1 [M+H]$^+$, 405.1 [M+Na]$^+$; IR: 3400, 3050, 2925, 2861, 1637, 1570, 1509 cm$^{-1}$; $^1$H NMR (DMSO-d$_6$, 400 MHz): δ 2.14 (s, 3H, CH$_3$), 2.62 (s, 8H, N—CH$_2$), 3.44 (s, 7-OH), 3.96 (s, 2H, 8-CH$_2$), 6.87 (s, 1H, 3-H), 7.46~7.54 (m, 3H, Ar—H), 8.01~8.02 (m, 2H, Ar—H), 8.11 (s, 6-OH), 12.64 (s, 1H, 5-OH).

Examples 2

Preparation of 5,6,7-trihydroxy-8-((4-(2-hydroxyethyl)piperazin-1-yl)methyl)-2-phenyl-4H-chromen-4-one [Hydroxyethylpiperazine Baicalein]

The mixture of Baicalein (27 g), methanol (350 ml), 37% formaldehyde solution (8.04 ml), 4-N-hydroxyethyl-piperazine (13.1 g) was stirred under for 4 hours at 51° C., then precipitates were removed by filtration and washed several times with methanol, after drying under reduced pressure at 55° C. to get the product as yellow solid 40.3 g of purity 98.5%. m.p.: 192° C. MS: (API-ES) m/z 413.3 [M+H]$^+$, 435.2 [M+Na]$^+$, 825.5[2M+H]$^+$, 847.5[2M+Na]$^+$; $^1$H NMR (DMSO-d$_6$/CFCOOD, 400 MHz): δ 8.18~8.19 (m, 2H, Ar-2',6'-H), 7.61~7.67 (m, 3H, Ar-3',4',5'-H), 7.09 (s, 1H, 3-H), 4.73 (s, 2H, CH$_2$), 3.76 (t, 2H, —CH$_2$—OH), 3.59-3.69 (m, 8H, CH$_2$), 3.33 (t, 2H, N—CH$_2$).

Examples 3

Preparation of 5,6,7-trihydroxy-8-((4-hydroxypiperidin-1-yl)methyl)-2-phenyl-4H-chromen-4-one [Hydroxypiperidin Baicalein]

The mixture of Baicalein (27 g), methanol (350 ml), 37% formaldehyde solution (8.04 ml), 4-hydroxy-piperidine (10.2 g) was stirred under for 4 hours at 51° C., then precipitates were removed by filtration and washed several times with methanol, after drying under reduced pressure at 55° C. to get the product as yellow solid 37.02 g of purity 99.2%. m.p.: 221° C. MS: (API-ES) m/z 384.2[M+H]$^+$, 767.5[2M+H]$^+$, 789.5 [2M+Na]$^+$; $^1$H NMR (DMSO-d$_6$, 400 MHz): δ 8.05~8.07 (m, 2H, Ar-2',6'-H), 7.58~7.59 (m, 3H, Ar-3',4',5'-H), 6.87 (s, 1H, 3-H), 4.17 (s, 2H, CH$_2$), 3.67 (m, 1H, CH), 2.68, 3.03 (m, 2H, CH$_2$), 2.71, 3.05 (m, 2H, CH$_2$), 1.52, 1.82 (m, 2H, CH$_2$), 1.53, 1.84 (m, 2H, CH$_2$).

Preparation of 6,7-trihydroxy-8-((4-hydroxypiperidin-1-yl)methyl)-2-phenyl-4H-chromen-4-one Mesylate The mixture of [6,7-trihydroxy-8-((4-hydroxypiperidin-1-yl)methyl)-2-phenyl-4H-chromen-4-one] (11.00 g), absolute alcohol (100 ml), mesylate acid 3.07 g, was stirred. The precipitates were collected, filtered, and washed several times with absolute alcohol, after drying under reduced pressure at 65° C. to get the product as yellow solid 13.40 g, m.p.: 243° C.

Examples 4

Preparation of 5,6,7-trihydroxy-8-((3-hydroxypyrrolidin-1-yl)methyl)-2-phenyl-4H-chromen-4-one [Hydroxylpyrrolidine Baicalein]

The mixture of Baicalein (27 g), methanol (350 ml), 37% formaldehyde solution (8.04 ml), 3-hydroxyl-pyrrolidine (8.8 g) was stirred under for 4 hours at 50° C., then precipitates were removed by filtration and washed several times with methanol, after drying under reduced pressure at 65° C. to get the product as yellow solid 36.0 g of purity 99.0%. MS: (API-ES) m/z 370.1[M+H]$^+$, 739.2 [2M+H]$^+$, 761.2[2M+Na]$^+$; $^1$H NMR (DMSO-d$_6$, 400 MHz): δ 8.05~8.07 (m, 2H, Ar-2',6'-H), 7.58~7.59 (m, 3H, Ar-3',4',5'-H), 6.87 (s, 1H, 3-H), 4.17 (s, 2H, CH$_2$), 3.32 (m, 1H, CH), 2.28, 2.53 (m, 2H, CH$_2$), 2.20, 2.30 (m, 2H, CH$_2$), 1.81, 1.62 (m, 2H, CH$_2$).

Examples 5

Preparation of 6-((4-methylpiperazin-1-yl)methyl)-5,7-dihydroxy-8-methoxy-2-phenyl-4H-chromen-4-one [Methylpiperazine Wogonin]

The mixture of Wogonin (28.4 g), methanol (350 ml), 37% formaldehyde solution (8.04 ml), 4-N-methyl-piperazine (10.1 g) was stirred under for 4 hours at 51° C., then precipitates were removed by filtration and washed several times with methanol, after drying under reduced pressure at 55° C. to get the product as orange red solid 38.6 g of purity 99.7%. m.p.: 179° C. MS: (API-ES) m/z 397.5 [M+H]$^+$, 419.5 [M+Na]$^+$, $^1$H NMR (DMSO-d$_6$/CF$_3$COOD, 400 MHz): δ 8.12~8.14 (m, 2H, Ar-2',6'-H), 7.64~7.66 (m, 3H, Ar-3',4',5'-H), 7.15 (s, 1H, 3-H), 4.44 (s, 2H, CH$_2$), 3.96 (s, 3H, 8-OCH$_3$), 3.43-3.74 (m, 8H, CH$_2$), 2.93 (s, 3H, N—CH$_3$).

Examples 6

Preparation of 6-((4-(2-hydroxyethyl) piperazin-1-yl)methyl)-5,7-dihydroxy-8-methoxy-2-phenyl-4H-chromen-4-one [Hydroxyethylpiperazine Wogonin]

The mixture of Wogonin (28.4 g), methanol (350 ml), 37% formaldehyde solution (8.04 ml), 4-N-hydroxyethyl-piperazine (13.1 g) was stirred under for 4 hours at 50° C., then precipitates were removed by filtration and washed several times with methanol, after drying under reduced pressure at 65° C. to get the product as yellow solid 41.7 g of purity 99.5%. MS: (API-ES) m/z 427.5[M+H]$^+$, 449.5[M+Na]$^+$; $^1$H NMR (DMSO-d$_6$/CF$_3$COOD, 400 MHz): δ 8.11~8.13 (m, 2H, Ar-2',6'-H), 7.62~7.67 (m, 3H, Ar-3',4',5'-H), 7.11 (s, 1H, 3-H), 4.45 (s, 2H, CH$_2$), 3.98 (s, 3H, 8-OCH$_3$), 3.78 (t, 2H, —CH$_2$—OH), 3.49-3.69 (m, 8H, CH$_2$), 3.36 (t, 2H, N—CH$_2$).

Examples 7

Preparation of 5,7-dihydroxy-6-((4-hydroxypiperidin-1-yl)methyl)-8-methoxy-2-phenyl-4H-chromen-4-one [Hydroxypiperidine Wogonin]

The mixture of Wogonin (28.4 g), methanol (350 ml), 37% formaldehyde solution (8.04 ml), 4-hydroxy-piperidine (10.2 g) was stirred under for 4 hours at 50° C., then precipitates were removed by filtration and washed several times with methanol, after drying under reduced pressure at 65° C. to get the product as orange red solid 38.5 g of purity 99.4%. MS: (API-ES) m/z 398.5 [M+H]$^+$ 420.5 [M+Na]$^+$; $^1$H NMR (DMSO-d$_6$, 400 MHz): δ 8.05~8.06 (m, 2H, Ar-2',6'-H), 7.60~7.61 (m, 3H, Ar-3',4',5'-H), 6.90 (s, 1H, 3-H), 3.94 (s, 2H, CH$_2$), 3.83 (s, 3H, 8-OCH$_3$), 3.65-3.67 (m, 1H, CH), 2.62, 2.98 (m, 4H, CH$_2$), 1.51, 1.83 (m, 4H, CH$_2$).

Examples 8

Preparation of 6-((bis(2-hydroxyethyl)amino)methyl)-5,7-dihydroxy-8-methoxy-2-phenyl-4H-chromen-4-one [Diethanolamin Wogonin]

The mixture of Wogonin (28.4 g), methanol (350 ml), 37% formaldehyde solution (8.04 ml), diethanolamine (10.5 g) was stirred under for 4 hours at 55° C., then precipitates were removed by filtration and washed several times with methanol, after drying under reduced pressure at 65° C. to get the product as yellow solid 39.3 g of purity 99.2%. MS: (API-ES) m/z 402.4[M+H]$^+$, 424.4[M+Na]$^+$; $^1$H NMR (DMSO-d$_6$, 400 MHz): δ 8.05~8.06 (m, 2H, Ar-2',6'-H), 7.60~7.61 (m, 3H, Ar-3',4',5'-H), 6.90 (s, 1H, 3-H), 3.94 (s, 2H, CH$_2$), 3.83 (s, 3H, 8-OCH$_3$), 3.63 (m, 4H, O—CH$_2$), 2.55 (m, 4H, N—CH$_2$).

Examples 9

Preparation of 6-((dimethylamino)methyl)-5,7-dihydroxy-8-methoxy-2-phenyl-4H-chromen-4-one [Dimethylamine Wogonin]

The mixture of Wogonin (28.4 g), methanol (350 ml), 37% formaldehyde solution (8.1 ml), 33% dimethylamine solution (13.6 g) was stirred under for 4 hours at 55° C., then precipitates were removed by filtration and washed several times with methanol, after drying under reduced pressure at 65° C. to get the product as yellow solid 32.7 g of purity 99.3%. MS: (API-ES) m/z 342.5[M+H]$^+$; $^1$H NMR (DMSO-d$_6$, 400 MHz) δ 8.03~8.04 (m, 2H, Ar-2',6'-H), 7.59-7.60 (m, 3H, Ar-3',4',5'-H), 6.81 (s, 1H, 3-H), 3.97 (s, 2H, CH$_2$), 3.82 (s, 3H, 8-OCH$_3$), 2.56 (s, 6H, CH$_3$).

Examples 10

Preparation of 5,7-dihydroxy-8-methoxy-2-phenyl-6-(pyrrolidin-1-ylmethyl)-4H-chromen-4-one [Pyrrolidine Wogonin]

The mixture of Wogonin (28.4 g), methanol (350 ml), 37% formaldehyde solution (8.1 ml), pyrrolidine (7.1 g) was stirred under for 4 hours at 55° C., then precipitates were removed by filtration and washed several times with methanol, after drying under reduced pressure at 65° C. to get the product as orange red solid 35.4 g of purity 99.1%. MS: (API-ES) m/z 368.5[M+H]$^+$, 390.5[M+Na]$^+$; $^1$H NMR (DMSO-d$_6$, 400 MHz) δ 8.03~8.04 (m, 2H, Ar-2',6'-H), 7.59~7.60 (m, 3H, Ar-3',4',5'-H), 6.79 (s, 1H, 3-H), 4.09 (s, 2H, CH$_2$), 3.81 (s, 3H, 8-OCH$_3$), 3.03 (s, 4H, CH$_2$), 1.90 (s, 4H, CH$_2$).

Examples 11

Preparation of 5,7-dihydroxy-8-methoxy-2-phenyl-6-(piperazin-1-ylmethyl)-4H-chromen-4-one [Piperazine Wogonin]

The mixture of Wogonin (28.4 g), methanol (350 ml), 37% formaldehyde solution (8.1 ml), piperazine (8.6 g) was stirred under for 4 hours at 55° C., then precipitates were removed by filtration and washed several times with methanol, after drying under reduced pressure at 65° C. to get the product as yellow solid 36.1 g of purity 99.1%. MS: (API-ES) m/z 383.5 [M+H]$^+$; $^1$H NMR (DMSO-d6, 400 MHz) δ 8.13~8.14 (m, 2H, Ar-2',6'-H), 7.64~7.66 (m, 3H, Ar-3',4',5'-H), 7.14 (s, 1H, 3-H), 4.43 (s, 2H, CH$_2$), 3.98 (s, 3H, 8-OCH$_3$), 3.36 (s, 4H, CH$_2$), 3.56 (s, 4H, CH$_2$), 1.25 (s, 1H, NH).

Examples 12

Preparation of 5,7-dihydroxy-8-methoxy-6-(morpholinomethyl)-2-phenyl-4H-chromen-4-one [Morpholine Wogonin]

The mixture of Wogonin (28.4 g), methanol (350 ml), 37% formaldehyde solution (8.1 ml), morpholine (8.7 g) was stirred under for 4 hours at 55° C., then precipitates were removed by filtration and washed several times with methanol, after drying under reduced pressure at 65° C. to get the product as yellow solid 36.3 g of purity 99.1%. MS: (API-ES) m/z 384.5[M+H]$^+$, 406.5[M+Na]$^+$; $^1$H NMR (DMSO-d$_6$, 400 MHz) δ 8.07~8.08 (m, 2H, Ar-2',6'-H), 7.61~7.63 (m, 3H, Ar-3',4',5'-H), 7.00 (s, 1H, 3-H), 3.87 (s, 3H, 8-OCH$_3$), 3.82 (s, 2H, CH$_2$), 3.65 (s, 4H, CH$_2$), 2.60 (s, 4H, CH$_2$).

Examples 13

Preparation of 5,7-dihydroxy-8-methoxy-2-phenyl-6-(thiomorpholinomethyl)-4H-chromen-4-one [Sulfurmorpholine Wogonin]

The mixture of Wogonin (28.4 g), methanol (350 ml), 37% formaldehyde solution (8.1 ml), sulfurmorpholine (10.3 g) was stirred under for 4 hours at 55° C., then precipitates were removed by filtration and washed several times with methanol, after drying under reduced pressure at 65° C. to get the product as yellow solid 37.6 g of purity 99.2%. MS: (API-ES) m/z 400.5[M+H]$^+$, 422.5[M+Na]$^+$; $^1$H NMR (DMSO-d6, 400 MHz) δ: 8.06~8.08 (m, 2H, Ar-2',6'-H), 7.61~7.63 (m, 3H, Ar-3',4',5'-H), 6.99 (s, 1H, 3-H), 3.87 (s, 3H, 8-OCH$_3$), 3.84 (s, 2H, CH$_2$), 2.86 (s, 4H, CH$_2$), 2.71 (s, 4H, CH$_2$).

Examples 14

Preparation of 5,7-dihydroxy-8-methoxy-2-phenyl-6-(piperidin-1-ylmethyl)-4H-chromen-4-one [Piperidine Wogonin]

The mixture of Wogonin (28.4 g), methanol (350 ml), 37% formaldehyde solution (8.1 ml), piperidine (8.5 g) was stirred under for 4.5 hours at 55° C., then precipitates were removed by filtration and washed several times with methanol, after drying under reduced pressure at 65° C. to get the product as yellow solid 35.3 g of purity 99.2%. MS: (API-ES) m/z 382.5 [M+H]+, 404.5[M+Na]+; $^1$H NMR (DMSO-d$_6$, 400 MHz) δ 8.05~8.06 (m, 2H, Ar-2',6'-H), 7.60~7.61 (m, 3H, Ar-3',4',5'-H), 6.89 (s, 1H, 3-H), 3.95 (s, 2H, CH$_2$), 3.83 (s, 3H, 8-OCH$_3$), 2.79 (s, 4H, CH$_2$), 1.64 (m, 4H, CH$_2$), 1.50 (m, 2H, CH$_2$).

We claim:

1. A series of *Scutellaria* flavonoid organic amine derivatives with the structures illustrated in the following scheme: wherein R$_6$ is OH and R$_8$ is N-2'-hydroxyethylpiperazinylmethyl, N-2'-mercapto-ethylpiperazinylmethyl, 4'-hydroxylpiperidinylmethyl, 4'-keto-piperidinylmethyl, 2'-hydroxymethylpyrrolidinylmethyl, 2'-hydroxylpyrrolidinylmethyl or bis(2'-hydroxyethyl)aminomethyl; or wherein R$_8$ is OCH$_3$ and R$_6$ is piperazinylmethyl, N-methylpiperazinylmethyl, N-2'-hydroxyethylpiperazinylmethyl, N-2'-mercapto-ethylpiperazinylmethyl, 4'-hydroxylpiperidinylmethyl, 4'-keto-piperidinylmethyl, 2'-hydroxymethylpyrrolidinylmethyl, 2'-hydroxylpyrrolidinylmethyl, bis(2'-hydroxyethyl)aminomethyl, dimethylaminomethyl, pyrrolidinylmethyl, piperidinylmethyl, N-morpholinomethyl or N-thiomorpholinomethyl

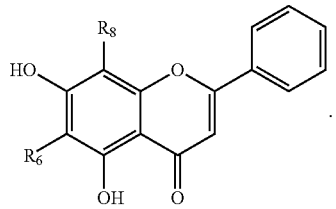

2. A series of *Scutellaria* flavonoid organic amine derivatives with the structures illustrated in the following scheme:

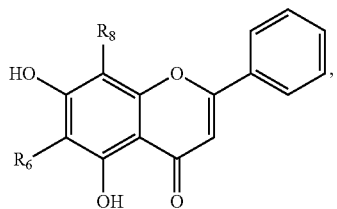

wherein R$_6$ is OH and R$_8$ is 4'-hydroxylpiperidinylmethyl, N-2'-hydroxyethylpiperazinylmethyl, N-2'-mercapto-ethylpiperazinylmethyl, 2'-hydroxylpyrrolidinylmethyl or bis(2'-hydroxyethyl)aminomethyl.

3. *Scutellaria* flavonoid organic amine derivatives of claim 1, wherein R$_8$ is OCH$_3$ and R$_6$ is N-2'-hydroxyethylpiperazinylmethyl, 4'-hydroxylpiperidinylmethyl, N-methylpiperazinylmethyl, 2'-hydroxylpyrrolidinylmethyl or bis(2'-hydroxyethyl)aminomethyl.

4. A series of *Scutellaria* flavonoid organic amine derivatives with the structures illustrated in the following scheme:

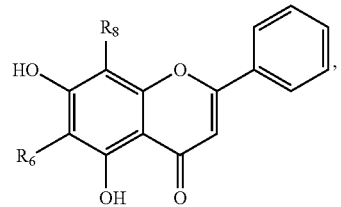

wherein R$_6$ is OH and R$_8$ is 4'-hydroxylpiperidinylmethyl, 2'-hydroxylpyrrolidinylmethyl or N-2'-hydroxyethylpiperazinylmethyl; or wherein R$_8$ is OCH$_3$ and R$_6$ is N-2'-hydroxyethylpiperazinylmethyl, 4'-hydroxylpiperidinylmethyl, 2'-hydroxylpyrrolidinylmethyl or bis(2'-hydroxyethyl)aminomethyl.

5. A process of making *Scutellaria* flavonoid organic amine derivatives of claim 1 wherein the steps are as follows: taking Baicalein or Wogonin as lead compound, mixting it with formaldehyde solution and organic amine compounds based on the molar ratio of 1:1-1.2:1-1.2, adding methanol of 10~40 times weight than baicalein or Wogonin, and stirring at 50-70° C. for 1-6 hours, filtering the sediment and washing with methanol of 1~20 times weight than baicalein or Wogonin, and then drying so as to get the product with a content of not less than 97% (weight).

6. The process of claim 5, wherein when Baicalein is used, the organic amine is piperazine, hydroxyethylpiperazine ethanethiolpiperazine, hydroxyethylpiperazine piperidone, hydroxymethylpyrrolidine, hydroxylpyrrolidine or diethanolamine; when Wogonin is used, the organic amine is piperazine, methylpiperazine, hydroxyethylpiperazine ethanethiolpiperazine, hydroxylpiperidine, piperidone, hydroxymethylpyrrolidine, hydroxylpyrrolidine, diethanolamin, dimethylamine, pyrrolidine, piperidine, morpholine or sulfurmorpholine.

7. The *Scutellaria* flavonoid organic amine derivatives of claim 2, wherein R$_6$ is OH and R$_8$ is 4'-hydroxylpiperidinylmethyl, N-2'-hydroxyethylpiperazinylmethyl or 2'-hydroxylpyrrolidinylmethyl.

8. The *Scutellaria* flavonoid organic amine derivatives of claim 4, wherein R$_8$ is OCH$_3$ and R$_6$ is N-2'-hydroxyethylpiperazinylmethyl, 4'-hydroxylpiperidinylmethyl, 2'-hydroxylpyrrolidinylmethyl or bis(2'-hydroxyethyl)aminomethyl.

9. A composition comprising a *Scutellaria* flavonoid organic amine derivative according to claim 1.

10. A composition comprising a *Scutellaria* flavonoid organic amine derivative according to claim 2.

11. A composition comprising a *Scutellaria* flavonoid organic amine derivative according to claim 3.

12. A composition comprising a *Scutellaria* flavonoid organic amine derivative according to claim 4.

13. A composition comprising a *Scutellaria* flavonoid organic amine derivative according to claim 7.

14. A composition comprising a *Scutellaria* flavonoid organic amine derivative according to claim 8.

* * * * *